United States Patent [19]

Hosono

[11] 4,240,411
[45] Dec. 23, 1980

[54] DEVICE FOR SEALING AN ENDOSCOPE CHANNEL

[75] Inventor: Saburo Hosono, Hachioji, Japan

[73] Assignee: Olympus Optical Co., Ltd., Tokyo, Japan

[21] Appl. No.: 897,428

[22] Filed: Apr. 18, 1978

[30] Foreign Application Priority Data

Apr. 25, 1977 [JP] Japan .............................. 52/52438[U]

[51] Int. Cl.³ ............................................... A61B 1/00
[52] U.S. Cl. ....................................................... 128/4
[58] Field of Search ........................................ 128/3–8,
128/274, 240–241, 349 R, 349 B, 349 BV, 348,
350 R, 351; 215/311; 137/223; 251/9, 149.2,
149.7; 243/348–349; 277/207 R, 209

[56] References Cited

U.S. PATENT DOCUMENTS 4,014,048  3/1977  Rappleyea ............................ 137/223

FOREIGN PATENT DOCUMENTS 1226241  6/1963  Fed. Rep. of Germany .
  35387  11/1965 Fed. Rep. of Germany .............. 128/4
  34710   2/1970 Fed. Rep. of Germany .
 126844   5/1919 United Kingdom ....................... 128/7

Primary Examiner—Robert W. Michell
Assistant Examiner—Jeffrey W. Tayon

[57] ABSTRACT

A device for sealing an endoscope channel is provided in the operation section of an endoscope and comprises a hollow cylindrical member connected at one end to the proximal end of a channel disposed in the sheath of the endoscope and a tubular member of an elastic material disposed in the hollow cylindrical member and connected at one end sealingly to the other end of the hollow cylindrical member. The other end portion of the tubular member is bent to form a sealing portion which can prevent air introduced into a body cavity from flowing back therefrom through the channel.

7 Claims, 11 Drawing Figures

F I G. 4
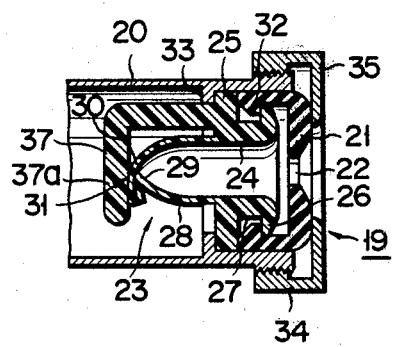
F I G. 5
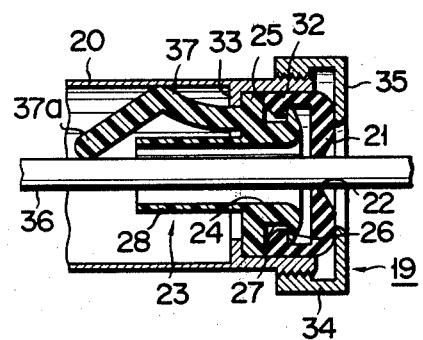
F I G. 6
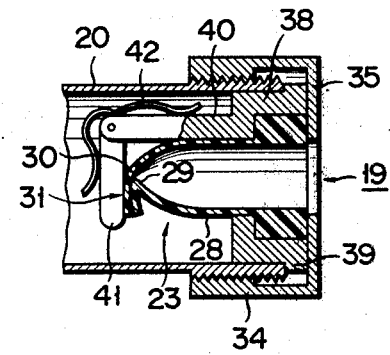
F I G. 7
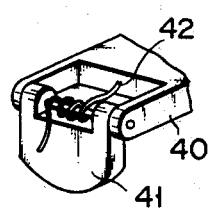

DEVICE FOR SEALING AN ENDOSCOPE CHANNEL

BACKGROUND OF THE INVENTION

This invention relates to a device for sealing an endoscope channel for preventing air from flowing back from a body cavity through the endoscope channel for allowing a medical instrument such as a forceps to be inserted into the body cavity.

It is necessary that an endoscope having an air channel should be provided with means for preventing air from flowing back from a body cavity through an operation channel and or a water channel.

To avoid back-flow of air, an elastic ring with a slit has been attached to the inlet of an operation channel, and a cap has been used to cover the inlet of a water channel. A medical instrument inserted into the operation channel is resiliently pressed by the ring in the slit, thereby to achieve sealing of the operation channel. However, every time the medical instrument is inserted into, or pulled out from, the operation channel, it strongly rubs the ring in the slit. As the ring is repeatedly rubbed in this manner, it is gradually worn out to have its slit broadended. Consequently, the sealing of the operation channel would not be maintained. Further, the cap should be removed from the inlet of the water channel when water is to be supplied through the water channel and should be attached to the inlet of the water channel when the water supply is completed, rendering the endoscope operation cumbersome. In addition, the cap, once removed, would probably be lost.

SUMMARY OF THE INVENTION

An object of this invention is to provide a device for sealing an endoscope channel, which is provided at the inlet of an endoscope channel and which is sufficiently durable and achieves a good sealing of the endoscope channel.

Another object of this invention is to provide a device for sealing an endoscope channel, which can be easily replaced.

According to this invention, there is provided a device for sealing an endoscope channel which comprises a hollow cylindrical member connected at one end to the proximal end of a channel in an endoscope and a tubular member of an elastic material disposed in the hollow member, said tubular member having one end connected to the other end of the hollow member and having a portion thereof bent to form a sealing portion.

While medical instrument such as a forceps is inserted in the channel, the sealing portion of the tubular member remains closed, thus preventing air from flowing back through the channel from a body cavity. When a medical instrument is inserted into the channel, the sealing portion is straightened with a relatively small force. The friction between the sealing portion and the medical instrument is therefore small. Thus, the life of the tubular member is lengthened.

The sealing portion of the tubular member may be formed by permanently bending a portion of the tubular member or by resiliently bending the same by means of another member.

In the other end of the hollow cylindrical member, there may be provided a connection ring of an elastic material which has an opening slightly smaller than the diameter of the medical instrument to be inserted into the channel and coaxially with the tubular member. Since the connection ring constricts the medical instrument in the opening, the sealing of the channel is secured during the insertion of the medical instrument.

When the tubular member and the connection ring are made detachable from the hollow member, they can be more easily replaced or washed than otherwise.

This device may be employed in an operation channel and/or a water channel formed in an endoscope.

BRIEF DESCRIPTION OF THE DRAWINGS

FIG. 4 is a cross sectional view of another embodiment of this invention, with no medical instrument inserted:

FIG. 5 is a cross sectional view of a further embodiment of this invention, with a medical instrument inserted.

FIG. 6 is a cross sectional view of still another embodiment of this invention;

FIG. 7 shows a blocking means comprising a spring and a blocking plate, both provided in the embodiment shown in FIG. 6;

DESCRIPTION OF THE PREFERRED EMBODIMENTS

Figure 1:
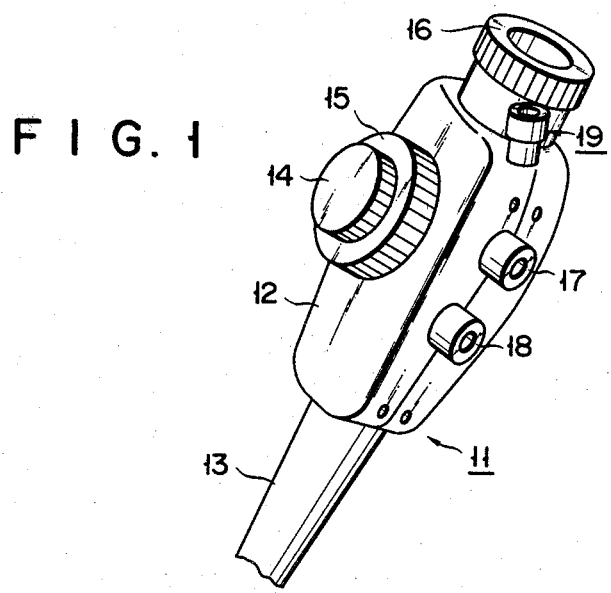
FIG. 1 is a perspective view of the main part of an endoscope to which the device according to this invention is applied.

In the figures, like reference numerals denote like or corresponding parts.

FIG. 1 shows an endoscope 11 to which this invention is applied. The endoscope 11 comprises an operation section 12 and a sheath 13 having its proximal end connected to the operation section 12. The operation section 12 is provided with remote control knobs 14 and 15 for bending the distal end portion of the sheath 13 in a desired direction through a desired angle. The operation section 12 is further provided with an eyepiece or ocular portion 16, an air inlet 17, a water inlet 18 and a sealing device 19. At the eyepiece 16 the interior of a body cavity is observed through a viewing window (not shown) provided at the distal end portion of the sheath 13. The air inlet 17 and the water inlet 18 are connected to the proximal end of an air channel (not shown) and the proximal end of a water channel (not shown), respectively. The air and water channels lengthwise extend in the sheath 13. The sealing device 19 communicates with an operation channel (not shown) into which a medical instrument such as a forceps is to be inserted.

Figure 2:
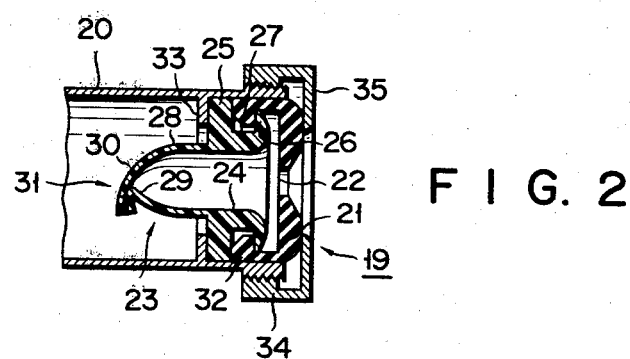
FIG. 2 is a cross sectional view of an embodiment of this invention, showing no medical instrument inserted.

As shown in FIG. 2, the sealing device 19 has a metallic hollow cylindrical member 20, one end of which protrudes outwardly from the upper end portion of the operation section 12 and the other end of which is connected to the proximal end of the operation channel. In the protruding end portion of the cylindrical member 20 there is forcibly fitted a connector ring 21 which is made of an elastic material such as rubber and which has an opening 22 slightly smaller than the diameter of the medical instrument 36 which will be described later. The sealing device 19 is provided with a tubular member 23 made of an elastic material such as elastic plastics. The tubular member 23 comprises two flanges 25 and 26, an annular engaging portion 24 having an annular groove 27 formed between the flanges 25 and 26, and a tubular portion 28 formed integrally with the sealing portion 24. Substantially one half 29 of the circumference of the free end portion of the tubular portion 28 is permanently bent in the form of inverted V, and substantially the other half 30 of the circumference of the free end portion is curved towards the former half 29 so as to make a sealing contact with the latter half 29. These halves 29 and 30 of circumference of the free end portion of the tubular portion 28 constitute a sealing portion 31.

The hollow cylindrical member 20 has an inwardly extending rim 33, and the connector ring 21 has an inwardly extending flange 32. The connector ring 21 and the tutular member 23 are put together outside the hollow cylindrical member 20, so that the flange 32 is snapped into the annular groove 27. Thereafter, the connector ring 21 and the tubular member 23 are forcibly pushed into the hollow cylindrical member 20 until the flange 25 of the tubular member 23 comes into contact with the rim 33 of the hollow cylindrical member 20.

In such a condition that a medical instrument is not inserted into the tubular member 23 as shown in FIG. 2, the closed sealing portion 31, the connector ring 21 and the rim 33 cooperate to completely seal the hollow cylindrical member 20 from the atmosphere (i.e., the outside of the cylindrical member 20).

An end ring 34 is threadably mounted on the protruding end of the hollow cylindrical member 20. The end ring 34 has an inwardly extending flange 35 which engages the connector ring 21, thereby to prevent the connector ring 21 and the tubular member 23 from being removed out of the hollow cylindrical member 20. When the end ring 34 is removed from the hollow cylindrical member 20, the connector ring 21 and the tubular member 23 can be taken out. Thus, the ring 21 and/or the tubular member 23 can be washed or replaced by a new one.

Figure 3:
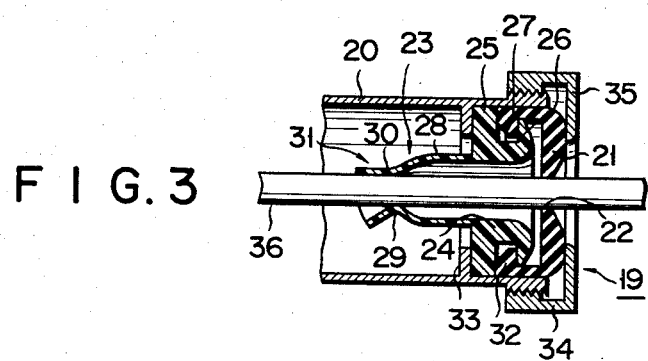
FIG. 3 is a cross sectional view of the device shown in FIG. 2, with a medical instrument inserted.

In FIG. 3, an elongate, thin medical instrument 36 such as a forceps is inserted into the sealing device 19. The instrument 36 first passes through the opening 22 of the connector ring 21. Then it pushes and opens the sealing portion 31 of the tubular member 23, and finally goes into an operation channel (not shown) in the endoscope 11. The resilient force of the sealing portion 31 is not so strong, and the instrument 36 can open it by a small thrust force. Accordingly, the friction between the instrument 36 and the inner surface of the sealing portion 31 is so small that the sealing portion 31 will not be worn out or damaged. This serves to lengthen the life of the tubular member 23.

Once the medical instrument 36 has been inserted into the operation channel, both halves 29 and 30 of the sealing portion 31 closely fit onto the outer periphery of the instrument 36 as shown in FIG. 3, and the interior of the hollow cylindrical member 20 remains sealed from the interior of the tubular member 23. The opening 22 of the connector ring 21, which is smaller than the diameter of the instrument 36 serves to maintain the sealing, even if a gap should be formed between the instrument 36 and the sealing portion 31 during the insertion of the instrument 36. After the instrument 36 is pulled out from the operation channel, the sealing portion 31 takes the folded form as shown in FIG. 2, thus maintaining the sealing of the interior of the channel from the atmosphere.

The sealing device 19 shown in FIG. 4 is identical with the embodiment of FIGS. 2 and 3 except that its tubular member 23 has an L-shaped arm member 37 which is formed integrally with the tubular member 23 so as to protrude from a flange 25 toward the sheath and is made of the same material as that of the tubular member 23. When a medical instrument is not inserted into the tubular member 23, the bent end portion 37A of the arm member 37 presses the sealing portion 31 of the tubular member 23 and closes it firmly. Thus, the sealing effect is much enhanced.

The sealing device 19 shown in FIG. 5 is similar to the embodiment of FIG. 4 except that the whole length of its tubular member 23 extends straight when a medical instrument 36 inserted into the tubular member 23 pushes the bent end portion 37A of an L-shaped arm member 37 away from the tubular member 23. After the medical instrument 36 is withdrawn from the tubular member 23, the arm 37 presses the free end portion of the tubular member 23 and forcibly folds it to seal the tubular member 23 from the atmosphere.

As a medical instrument 36 is inserted into the tubular member 23, the forward end of the medical instrument 36 opens the sealing portion 31 and at the same time pushes the end portion 37a of the arm member 37 toward the operation channel, and finally the lateral side of the medical instrument 36 moves the end portion 37a away from the tubular portion 28 of the tubular member 23. The tubular portion 28 extends straight as shown in FIG. 5 without being obstructed by the arm member 37. Thus, the medical instrument 36 does not contact the tubular member 23 while the medical instrument 36 is reciprocated and/or turned in the operation channel, thereby to ensure the prolonged life of the tubular member 23.

A sealing device 19 as shown in FIG. 6 comprises a hollow cylindrical member 20, a tubular member 23, an end ring 34 screwed on the cylindrical member 20 and a connector ring 38 having an outward extending flange 39 disposed between the proximal end of the cylindrical member 20 and the flange 35 of the end ring 34. The connector ring 38 is made of a metal and further provided with arms 40 which extend toward an operation channel. As shown in FIG. 7, a blocking plate 41 is hinged to the free ends of the arms 40 and is biased by a spring 42 so as to urge and fold the free end portion of the tubular member 23 to form a sealing portion 31 when a medical instrument such as a forceps is not inserted into the sealing device 19. The other portions of the device 19 are constructionally similar to those the embodiment of FIGS. 4 and 5.

In the embodiment of FIGS. 4 and 5, repeated insertion of the medical instrument into the operation channel tends to induce the fatigue of the bent portion of the arm member 37 with the result that the arm member 37 can no longer fold the end portion of the tubular portion 28. In order to restore the biasing force of the arm member 37, the tubular member 23 formed with the arm member 37 must be replaced by a new one. With the blocking means of the embodiment of FIGS. 6 and 7, however, fatigue occurs only in the spring 42 (though the spring 42 is less subjected to fatigue than the plastic arm member 37 in FIGS. 4 and 5). Thus the full recovery of the biasing force against the blocking plate 41 can be attained only by replacing the spring 42 with a new one.

Figure 8:
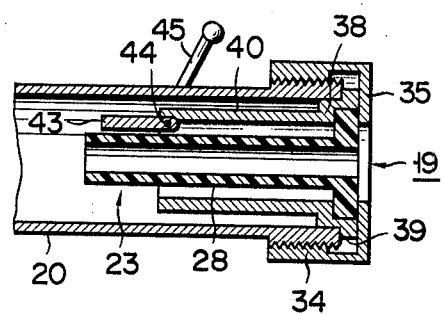
FIG. 8 is a cross sectional view of a further embodiment of this invention.
Figure 9:
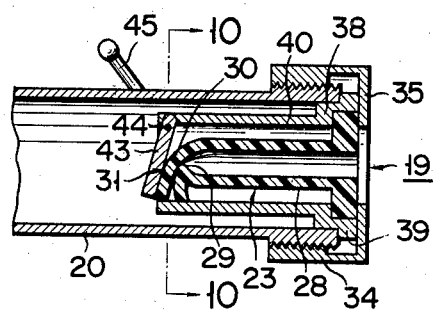
FIG. 9 shows a cross sectional view of still further embodiment of this invention.
Figure 10:
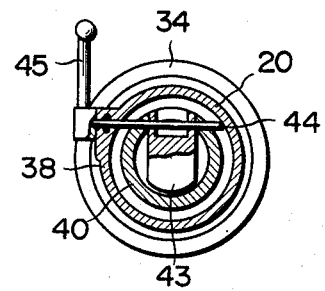
FIG. 10 is a sectional view of the embodiment shown in FIG. 9, taken along line 10—10 in FIG. 9 and showing a lever and a member for forming a sealing portion.

The sealing device 19 shown in FIGS. 8, 9 and 10 is similar in construction to the embodiment of FIGS. 6 and 7, except for the following points. First, a blocking plate 43 is hinged by a pin 44 to the free ends of hollow cylindrical arm 40 of a connector ring 38 with the both ends of the pin 44 pivoted to the connector ring 38. Second, a lever 45 is fastened to one end of the pin 44 at the outside the hollow cylindrical member 20 as shown in FIG. 10.

Figure 11:
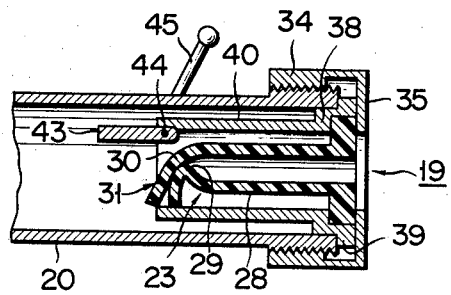
FIG. 11 is a cross sectional view of still further embodiment of this invention.

When the lever 45 is turned clockwise in FIG. 11, the blocking plate 43 is positioned substantially parallel to the axis of the tubular portion 28, thus permitting the tubular portion 28 to extend straight. When the lever 45 is moved counterclockwise as shown in FIG. 9, the blocking plate 43 is disposed substantially perpendicular to the axis of the tubular portion 28 and folds the free end portion of the tubular member 23, thus forming a sealing portion 31 in the similar way as shown in FIGS. 4 and 6. The sealing portion 31 is formed only when required, and the service life of the tubular member 23 becomes far longer than otherwise.

The sealing device 19 shown in FIG. 11 is identical with the embodiment of FIGS. 8, 9 and 10, except that the free end portion of the tubular member 23 is permanently bent to form a sealing portion 31 in the same manner as in the embodiment of FIGS. 2 and 3. Thus, the device 19 always effects sealing between the atmosphere and an operation channel (not shown) even if the blocking plate 43 lies in such a position as shown in FIG. 11. When the lever 45 is moved counterclockwise, the blocking plate 43 is pressed against the sealing portion 31, whereby the sealing between the atmosphere and the operation channel is more secured.

It should be noted that the sealing device can be applied to a water channel in the endoscope.

From the above description, it is easily understood that the sealing device unfailingly prevents air in the body cavity from flowing back through channels in an endoscope when the sealing device is provided in each channel.

What is claimed is:

1. In an endoscope having an operation section, an elongated sheath which has a proximal end connected to said operation section and in which channels each having two ends are formed, and a sealing device which is disposed in said operation section and which communicates with the corresponding channel, the improvement wherein said sealing device comprises a hollow cylindrical member having two ends, one end being connected to one of said two ends of the corresponding channel and a tubular member of an elastic material having two ends, one end being connected to the other end of said hollow cylindrical member and a portion adjacent to the other end of the tubular member which forms a sealing portion comprising a first part formed by substantially one half of the circumference of said portion adjacent to the other end of said tubular member and a second part formed by substantially the other half of said circumference, said first part being folded and said second part being sealingly pressed against said first part.

2. The sealing device according to claim 1, wherein said hollow cylindrical member is provided therein with a blocking means for normally resiliently pressing said sealing portion.

3. The sealing device according to claim 2, wherein said blocking means comprises a substantially L-shaped arm member of an elastic material.

4. The sealing device according to claim 2, wherein said blocking means comprises a blocking plate pivotally movable in said hollow cylindrical member and adapted to normally press said sealing portion, and a spring for biasing said blocking plate toward said tubular member.

5. The sealing device according to claim 2, wherein said blocking means comprises a blocking plate pivotally movable in said hollow cylindrical member and adapted to normally press said sealing portion, and a lever connected to said blocking plate and operated at the outside of said hollow cylindrical member.

6. The sealing device according to claim 2, wherein said tubular member is straightened when said blocking means is moved away therefrom.

7. The sealing device according to claim 1, wherein said sealing portion is permanently folded.

* * * * *